United States Patent
Silva et al.

(10) Patent No.: US 10,661,059 B2
(45) Date of Patent: May 26, 2020

(54) STRETCHABLE-DIAMETER INSERTER AND METHODS

(71) Applicant: Merit Medical Systems, Inc., South Jordan, UT (US)

(72) Inventors: Pedro Silva, Novedrate (IT); Patrizia Pini, Novedrate (IT); Paolo Cremascoli, Novedrate (IT)

(73) Assignee: Merit Medical Systems, Inc., South Jordan, UT (US)

( * ) Notice: Subject to any disclaimer, the term of this patent is extended or adjusted under 35 U.S.C. 154(b) by 68 days.

(21) Appl. No.: 14/642,288

(22) Filed: Mar. 9, 2015

(65) Prior Publication Data

US 2015/0174376 A1    Jun. 25, 2015

Related U.S. Application Data

(63) Continuation of application No. 12/587,201, filed on Oct. 2, 2009, now Pat. No. 8,974,419.

(30) Foreign Application Priority Data

Oct. 22, 2008  (IT) .................................. MI08A1870

(51) Int. Cl.
  *A61M 25/06* (2006.01)
  *A61M 25/00* (2006.01)
  *A61B 17/34* (2006.01)

(52) U.S. Cl.
  CPC .... *A61M 25/0662* (2013.01); *A61M 25/0021* (2013.01); *A61M 25/0023* (2013.01);
  (Continued)

(58) Field of Classification Search
  CPC .. A61M 2025/0024; A61M 2025/0025; A61M 25/0102
  See application file for complete search history.

(56) References Cited

U.S. PATENT DOCUMENTS

| 4,738,666 A | * | 4/1988 | Fuqua | A61M 25/0023 604/103.05 |
| 4,961,731 A | * | 10/1990 | Bodicky | A61M 25/007 604/264 |

(Continued)

FOREIGN PATENT DOCUMENTS

IT    1393665    5/2012

OTHER PUBLICATIONS

Notice of Allowance dated Dec. 15, 2014 for U.S. Appl. No. 12/587,201.

*Primary Examiner* — Emily L Schmidt
(74) *Attorney, Agent, or Firm* — Stoel Rives LLP

(57) ABSTRACT

A stretchable-diameter inserter, for hemodynamic studies and related operations, is characterized in that it comprises an inserter tube, a hemostatic valve designed for preventing blood from exiting the patient toward the operator, a side line including a faucet, adapted to be used for performing blood taking and infusion operations and two dilatators: a first dilatator having a smaller cross-section and a second dilatator having a larger cross-section. The inserter tube is made of a rigid and flexible material with a substantially circular or oval contour, and comprises one or more longitudinally extending reduced thickness regions; each said reduced thickness region being folded on itself; the inner diameter therewith the tube is originally extruded is that desired for a maximum diameter configuration; the thus obtained extruded tube being then thermoformed so as to cause the reduced thickness region edges to be approached to one another thereby providing a minimum diameter tube; the thermoforming method so handling the reduced thickness region as to cause the tube material forming its thickness to be folded inward the tube, to allow the tube edges to move one another.

20 Claims, 10 Drawing Sheets

(52) U.S. Cl.
CPC ...... *A61B 17/3439* (2013.01); *A61M 25/0009* (2013.01); *A61M 2025/0024* (2013.01); *Y10T 156/1051* (2015.01)

(56) References Cited

U.S. PATENT DOCUMENTS

| | | | | |
|---|---|---|---|---|
| 5,997,508 | A | * | 12/1999 | Lunn ................. A61M 25/0662 604/164.08 |
| 6,090,072 | A | * | 7/2000 | Kratoska ............ A61B 17/3439 604/164.01 |
| 6,197,016 | B1 | * | 3/2001 | Fourkas ............. A61B 17/3462 604/248 |
| 8,974,419 | B2 | | 3/2015 | Pini et al. |
| 2002/0032459 | A1 | * | 3/2002 | Horzewski ......... A61B 17/3439 606/198 |
| 2005/0222576 | A1 | * | 10/2005 | Kick .................. A61B 17/3439 606/104 |
| 2006/0217755 | A1 | * | 9/2006 | Eversull ............. A61B 17/3439 606/191 |
| 2008/0243072 | A1 | * | 10/2008 | Jenson ................ A61M 25/09 604/103.14 |
| 2010/0094392 | A1 | * | 4/2010 | Nguyen ............... A61F 2/2427 623/1.11 |

\* cited by examiner

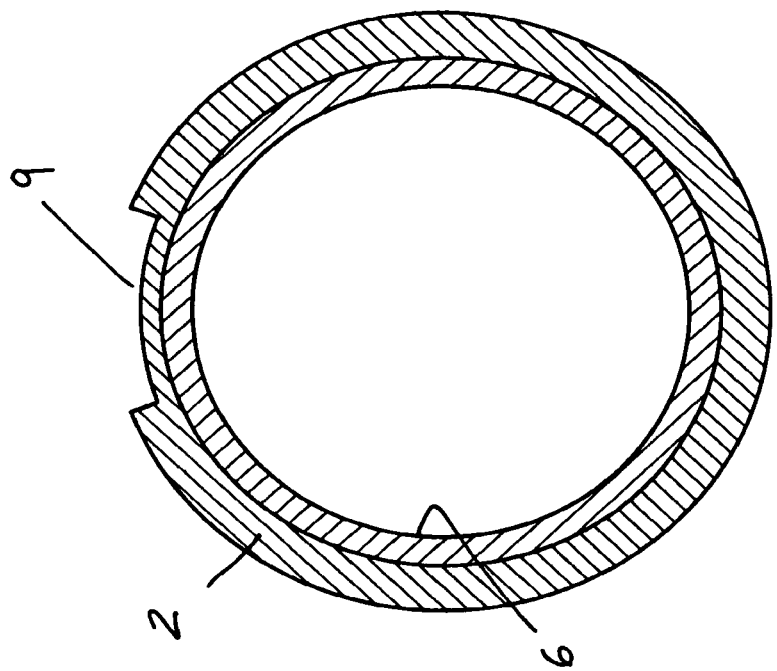
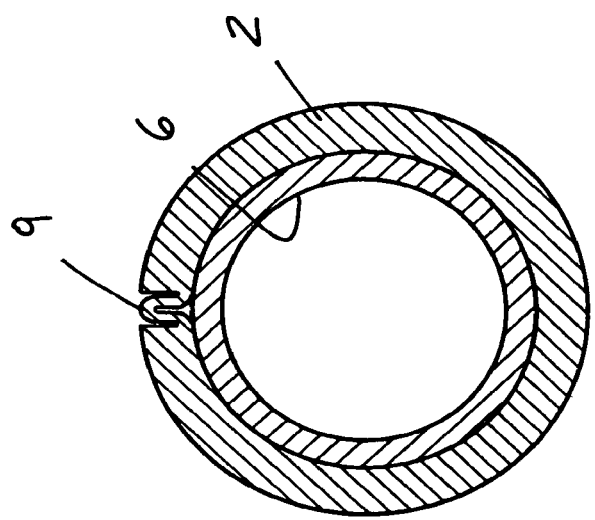
Fig. 4

STRETCHABLE-DIAMETER INSERTER AND METHODS

RELATED APPLICATIONS

This application is a continuation of co-pending U.S. patent application Ser. No. 14/587,201, filed Oct. 2, 2009, titled "STRETCHABLE-DIAMETER INSERTER FOR HEMODYNAMIC STUDIES AND RELATED OPERATIONS," which claims the benefit of Italian Patent Application No. MI2008A 001870, filed on Oct. 22, 2008, each of which is incorporated herein by reference in its entirety.

BACKGROUND OF THE INVENTION

The present invention relates to an inserter, designed to be used in hemodynamic studies and related operations.

As is known, in a surgical operation, the patient hematic flow is accessed by puncturing an artery vessel, typically a femoral or radial vessel, and the vessel being held in a pervious of patient condition by an inserter, which is a medical device to be used in surgical operations in general, for example during a hemodynamic monitoring, an electrocatheter implant, a diagnostic study procedure or any other desired surgical operating procedures, and is specifically designed to introduce, exchange and monitor other medical devices, for example catheters and electrodes, into a patient vessel.

An inserter, in particular, has generally a variable length, but a small size, for example from 15 to 90 cm for a femoral and radial artery, and is specifically selected based on its inner diameter, corresponding to the size of the device to be introduced thereinto.

The inserter, which is held at its target position through the overall duration of the surgical procedure, and also for several days after such a procedure, conventionally comprises a rigid low friction material extruded tube, usually made of FEP and PTFE, having a small thickness and a tapering end portion.

Some inserters, moreover, are structurally reinforced through their thickness by a metal armoring construction to prevent the inserter tube from bulging.

The proximal portion of the inserter is usually coupled to a hemostatic valve, or rigid plastic component including a silicone material diaphragm, designed for insulating the inserter from the encompassing outside environment, which valve, designed to prevent blood from exiting and air from entering the patient vessel, comprises a pre-cut silicone diaphragm for axially holding an auxiliary device which is thus "encompassed" by the silicone material to provide a tight sealing.

On a side of said valve and downstream thereof is furthermore provided a line contacting the patient blood for continuously monitoring its patient pressure.

The above inserter is generally installed or implanted by using the so-called Seldinger's technique.

According to this procedure, a patient vessel is punctured by a needle, and then into this needle a guide wire having a suitable length and adapted to be arranged at a target point of the vessel is introduced.

Then, the needle is withdrawn and on the guide the inserter-dilatator system is caused to slide.

The dilatator is a flexible tube, made of a low friction material, such as PTFE, comprising an elongated tip to facilitate the inserting operation, and has an outer diameter equal to the inner diameter of the inserter.

Then, a suitably designed proximal system allows the dilatator to be engaged in and disengaged from the inserter, after having withdrawn the latter, thereby, at the end of such an operation, only the inserter will be held in the patient vessel.

Accordingly, the inserter must have such a stiffness as to prevent the vessel from closing because of its resilient properties.

In this connection it should be pointed out that the above mentioned Seldinger's procedure allows the vessel to be opened by a dilating hole and not, as one could think, by a cut.

In other words, the above procedure exploits the deforming resilient capability of the vessel, and is also very useful for reclosing the vessel at the end of the operation, since an incision or cut would be much more difficult to heal than a hole; the vessel being closed by manually pressing it or by using specifically designed closure systems, such as percutaneous sutures or collagen based systems.

In the above mentioned operations, it is sometimes moreover necessary to change the inserter and replace it by a larger or smaller diameter one, for example in an implant procedure for implanting ventricular assistance systems, to allow an application of a larger diameter device.

At present, the above operations require the installed inserter to be removed, and repeat the Seldinger's procedure, to relocate said inserter.

SUMMARY OF THE INVENTION

Accordingly, the aim of the present invention is to provide an inserter adapted to be used in hemodynamic studies and related operations, which allows the above mentioned drawbacks of the prior art to be overcome.

Within the scope of the above mentioned aim, a main object of the invention is to provide such an inserter adapted to reduce the material amount necessary for performing the related procedure.

Another object of the invention is to provide such an inserter allowing to also reduce the operation time.

Yet another object of the present invention is to provide such an inserter also adapted to reduce bleeding due to replacement operations.

Yet another object of the present invention is to provide such an inserter also adapted to reduce any risks associated with a relocating of said inserter.

Yet another object of the present invention is to provide such an inserter also adapted to reduce any vessel traumas because of an inserter replacement operation, as necessary in using conventional inserters.

Yet another object of the present invention is to provide such an inserter facilitating a closure of the puncture situ.

Yet another object of the present invention is to provide such an inserter device which, owing to its specifically designed constructional features, is very reliable and safe in operation.

Yet another object of the present invention is to provide such an inserter allowing a different diameter catheter, such as a small diameter catheter for performing diagnostic assays and a large diameter catheter for performing revascularization operations to be easily fixed therein.

According to one aspect of the present invention, the above mentioned aim and objects, as well as yet other objects, which will become more apparent hereinafter, are achieved by an inserter, specifically designed to be used in hemodynamic studies and related operations, characterized in that said inserter comprises a rigid and flexible material tube having a substantially circular or ovaled contour, said tube comprising one or more longitudinally extending reduced thickness regions, each said reduced thickness region being folded on itself; the inner diameter therewith said tube being originally extruded being the diameter desired in a maximum diameter configuration of said tube; said extruded tube being so thermoformed as to cause the reduced thickness region edges to approach one another thereby providing a minimum diameter configuration tube; the thermoforming method including handling said reduced thickness region thereby causing the tube material forming the thickness of said reduced thickness region to be folded to the inside of said tube thereby allowing said tube edge to approach one another.

BRIEF DESCRIPTION OF THE DRAWINGS

Further characteristics and advantages of the present invention will become more apparent hereinafter from the following detailed disclosure of a preferred, though not exclusive, embodiment of the invention, which is illustrated, by way of an indicative, but not limitative, example in the accompanying drawings, where:

FIG. 4 is a further cross-sectional view of the tube forming the inserter body, with a dilatator engaged therein, respectively at a minimum and a maximum diameter position;

DESCRIPTION OF THE PREFERRED EMBODIMENTS

With reference to the number references of the above mentioned figures, the inserter according to the present invention, which has been generally indicated by the reference number 1, comprises an inserter tube 2, constituting an implantable inserter portion, a hemostatic valve 3, adapted to prevent the patient blood from exiting the operator, and a side line 4, including a related faucet or cock 5, for performing blood taking or infusing operations, or any other desired measurement procedures.

Figure 1:
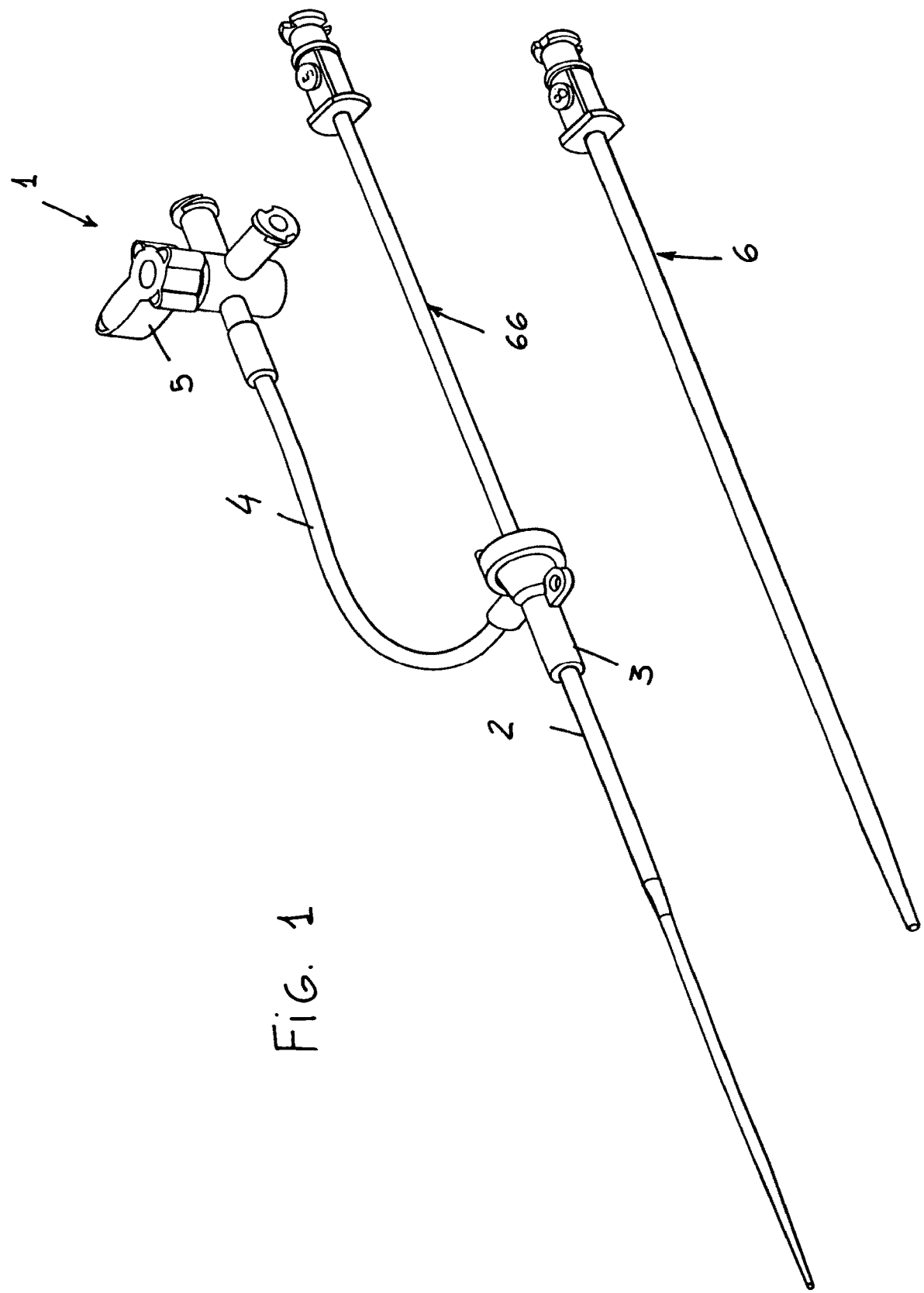
FIG. 1 is a perspective view showing an inserter according to the present invention, as pre-assembled on a dilatator, in particular of a small size, and with an adjoining second dilatator, having a maximum use diameter.

FIG. 1 shows the inserter 1 in a pre-assembled condition, in which it is preassembled on a dilatator 66, in particular a small-size dilatator, and, on a side of this figure, is shown a second dilatator 6 having a maximum usable diameter.

Figure 2:
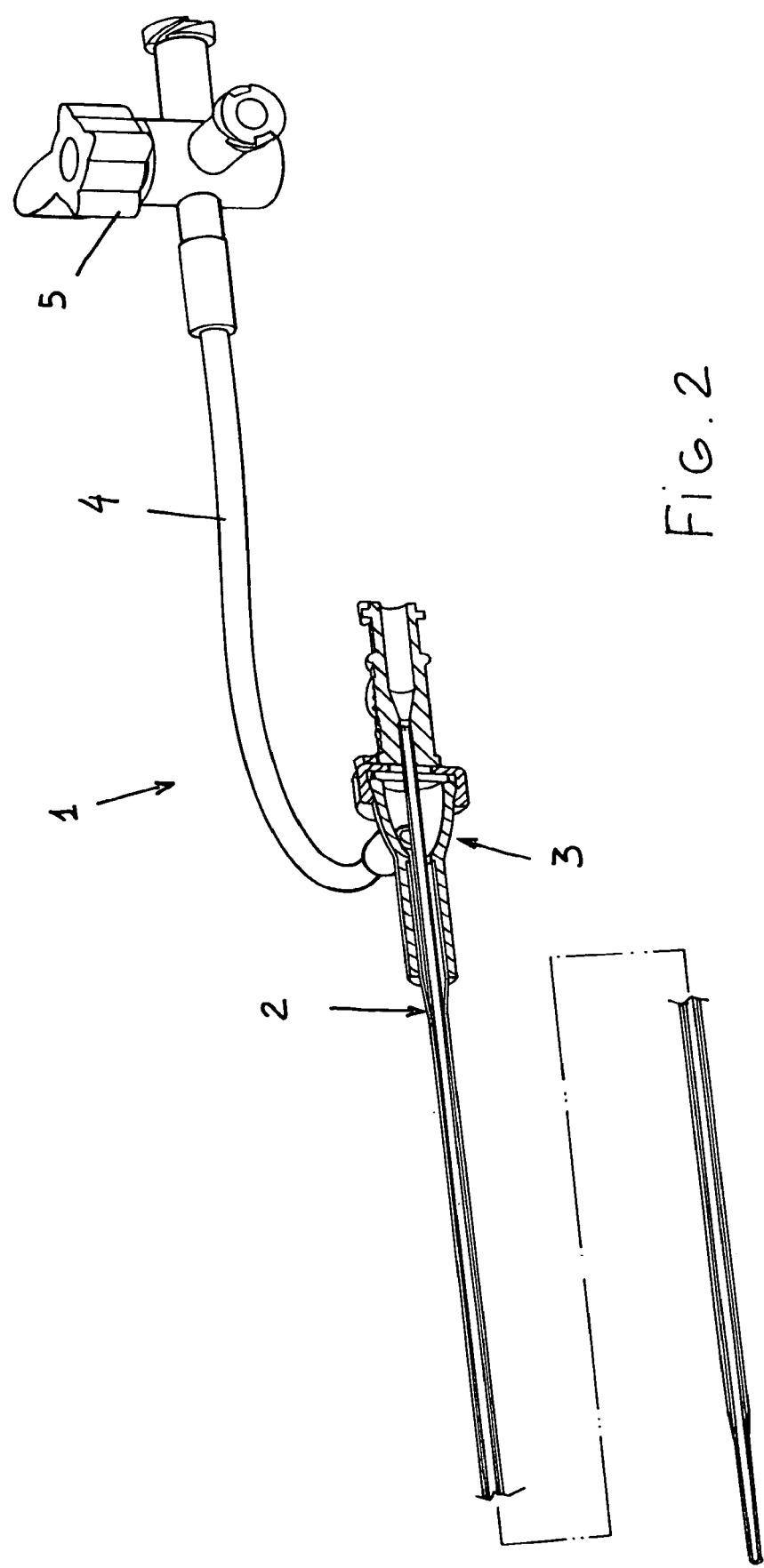
FIG. 2 is a cross-sectional view showing the dilatator-introducer assembly.
Figure 3:
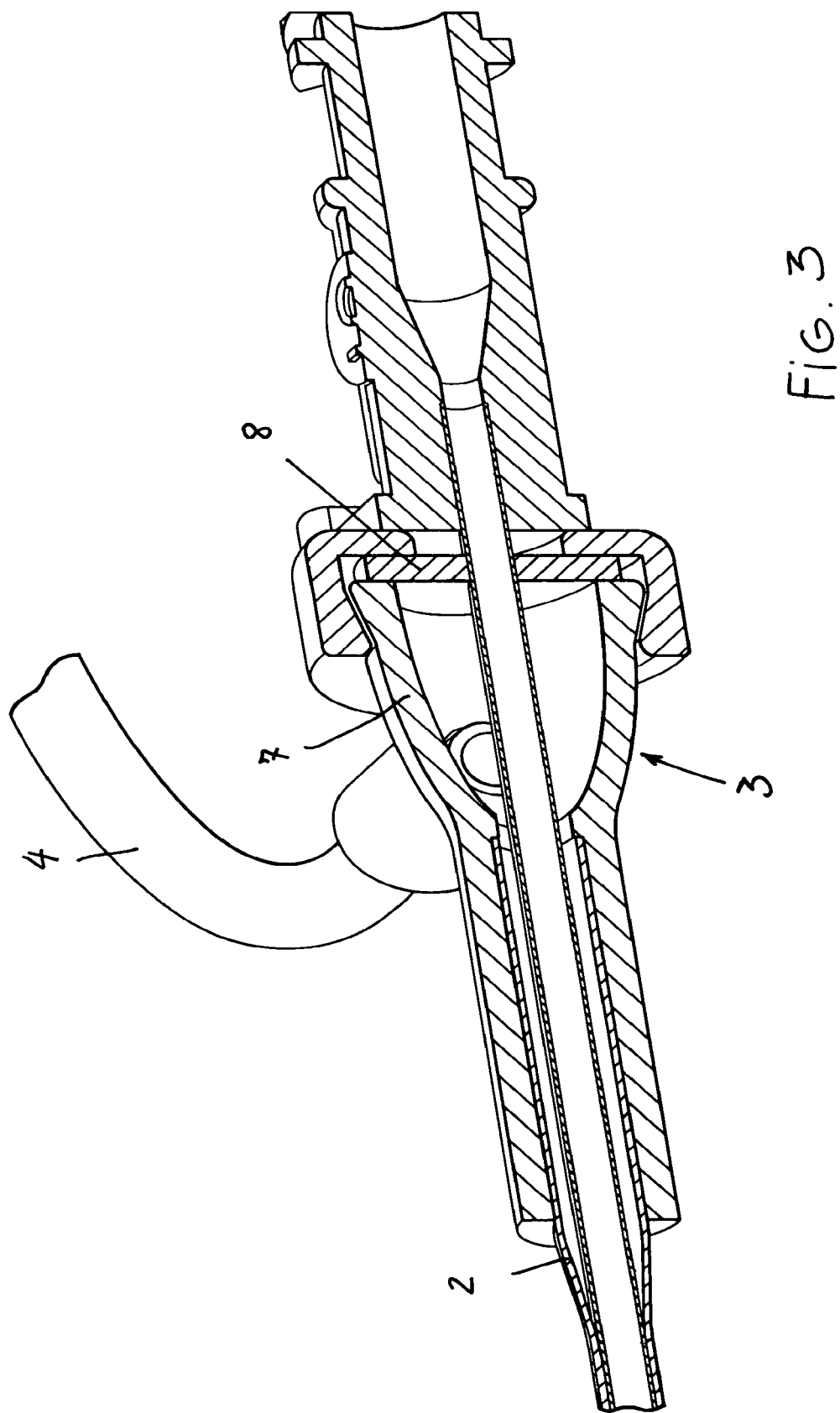
FIG. 3 is a perspective view, on an enlarged scale, of a hemostatic valve and a sealing region with a minimum diameter inserter tube.

In FIG. 2, the inserter tube has its minimum diameter configuration, the inner diameter of the valve being preset for fitting the tube maximum diameter, thereby the introduce tube, will have, at the outlet of said valve, a transition conic arrangement 7 between the maximum (inside) diameter and minimum (outside) diameter.

The hemostatic valve 3, shown in figure substantially comprises a connector in which a diaphragm 8 including a silicone material disc or membrane is arranged.

As is known, silicone is a soft and cohesive elastomeric material.

The diaphragm 8 is engaged in the valve, and the possibility of further engaging and removing any desired device without causing blood to leak, is due to a pre-incision made of a plurality of cuts adjoining at the central portion of the diaphragm (either three, four or five cuts, thereby providing a star arrangement).

At a rest condition thereof, the diaphragm 8 is in a closed condition.

As a device is caused to pass through the valve 3, it is conveyed through the cuts of the diaphragm 8.

In particular, said device may comprise a vascular catheter or a dilatator, and, accordingly, has a substantially tubular configuration.

The diaphragm 8 material will be arranged so as to perfectly adhere to the outer surface of the device, for example the dilatator 6 and dilatator 66.

Thus, between the two materials no vacuum region is formed, that is no gap between the diaphragm and body passing therethrough.

In using a vascular inserter, such a cohesive property would have a basic importance for preventing any blood leakages from occurring from the patient to the encompassing environment, or for preventing air from entering the circulatory system of the patient, with a consequent risk of embolism.

The valve is laterally coupled on the outer line 4, comprising a PVC or PU tube ending with the three-way faucet or cock 5.

This line 4 is arranged downward of the inner diaphragm 8 and, accordingly, directly communicates with the body of the inserter 1 and, accordingly, with the vessel blood.

This line 4 is used for performing patient blood taking and infusing operations, or for performing other monitoring or measuring procedures.

The valve 3 is line coupled to the inserter body 2, which represents the implanting part of the device.

The tube 2 forming the inserter body, in particular, is the core of the present invention.

The tube 2 is made of a rigid, flexible material, and preferably a low friction material, such as PE.

The tube 2 is extruded with a specifically designed contour, shown in FIG. 4, i.e. with a circular contour including one or more reduced thickness regions 9, said reduced thickness regions 9 being folded on themselves, as shown on the left of the figure (the type of folding shown in this figure being herein indicative and not limitative).

The inner diameter to which the tube 2 is originally extruded is that to be achieved in the maximum diameter configuration, for example 2.7 mm, that is 8 Fr, whereas the wall thickness is as thin as possible, for example 0.1 mm.

The extruded material is then thermoformed so as to cause the edges of the regions 9 to be moved toward one another thereby providing a minimum diameter configuration tube, for example of 1.7 mm, that is 5 Fr.

The thermoforming method provides to so handle the region of the region or recess 9 to cause the tube thickness material to be folded inward the tube, thereby causing the two edges to move to one another.

The length of the said recessed region 9 corresponding to the length of the circular crown due to a difference between the maximum diameter inserter and the circumference of the rest diameter inserter ($\Delta\zeta=\zeta_{FINAL}-\zeta_{INITIAL}=2\pi\ (R_{FINAL}-R_{INITIAL})$).

It also represents the material amount which is thermoformed and arranged in the tube.

The thus processed tube will have a circular or slightly ovaled contour, with one or more "channel", generally indicated by the reference number 10 extending outward and through the longitudinal extension or length thereof.

It has been found that said channel elements 10 prevent the patient blood from outward leaking, due to any capillarity trend.

Depending on the required length, one or more enlargement or stretching regions are provided in the tube 2.

In a case in which a plurality of recessed regions are provided, a non diametrically opposite arrangement is further provided, for preventing the tube from becoming brittle as it is curved.

The tube 2 can also comprise several materials (a multilayer tube) or a single material with different hardness properties, for example a softer material to be used for the tube inner part and a harder material to be used for the tube outer part, or a very slippery material (such as FEP) may form the inside of the tube and a more ductile material may form the outside of said tube.

Moreover, the tube 2 may be lined by a hydrophilic substance, or any substances adapted to reduce friction between said tube and the devices being conveyed therethrough.

Figure 5:
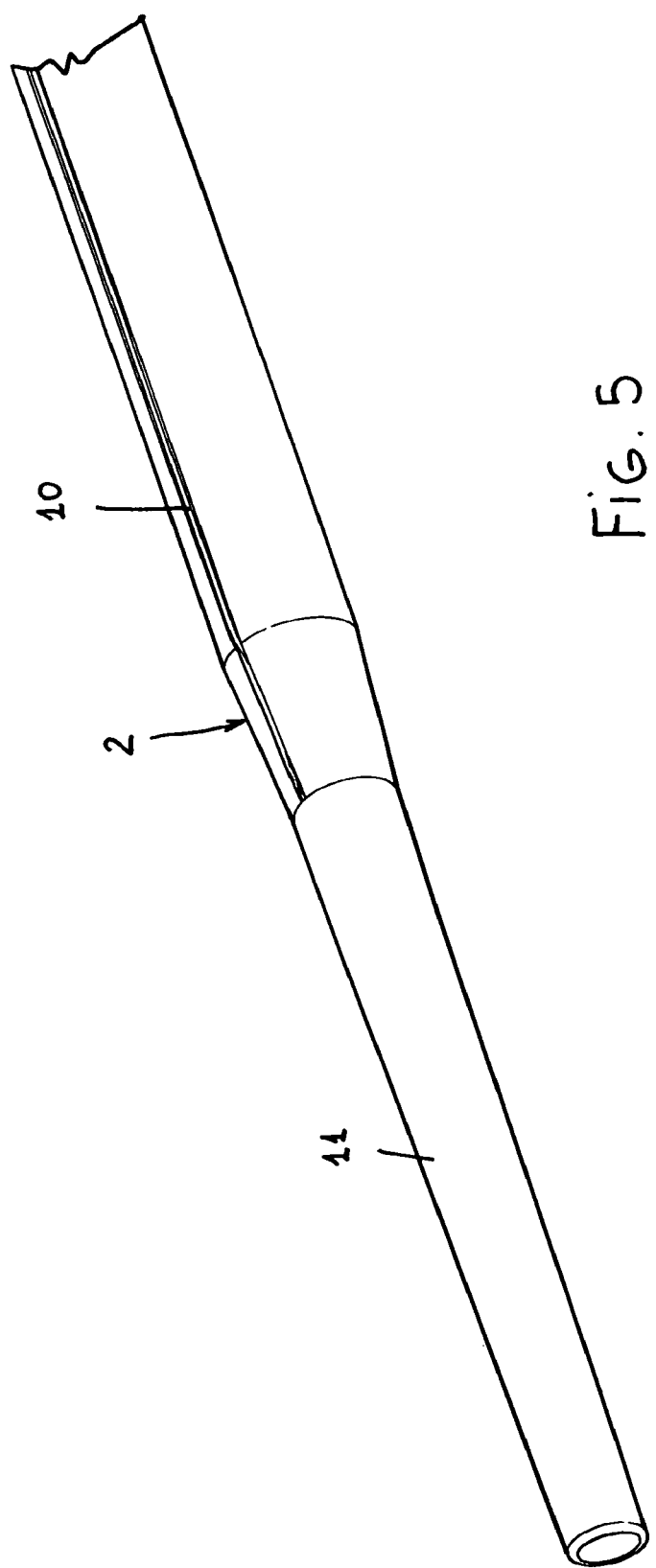
FIG. 5 is a perspective view of the inserter tube, clearly showing the tapering tip thereof as well as a channel element.
Figure 6:
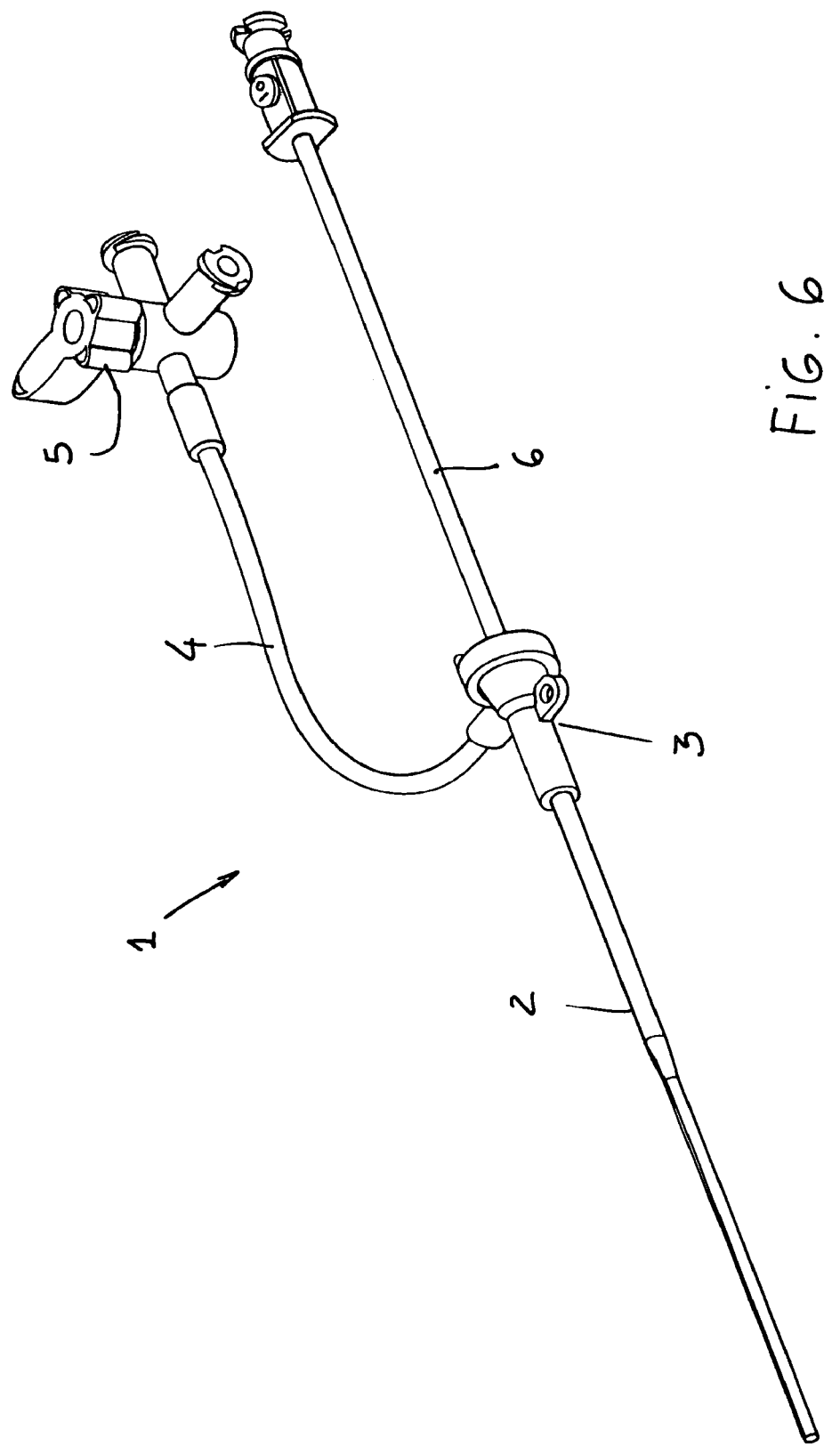
FIG. 6 show a first operating step for engaging or introducing the dilatator into the inserter tube.
Figure 7:
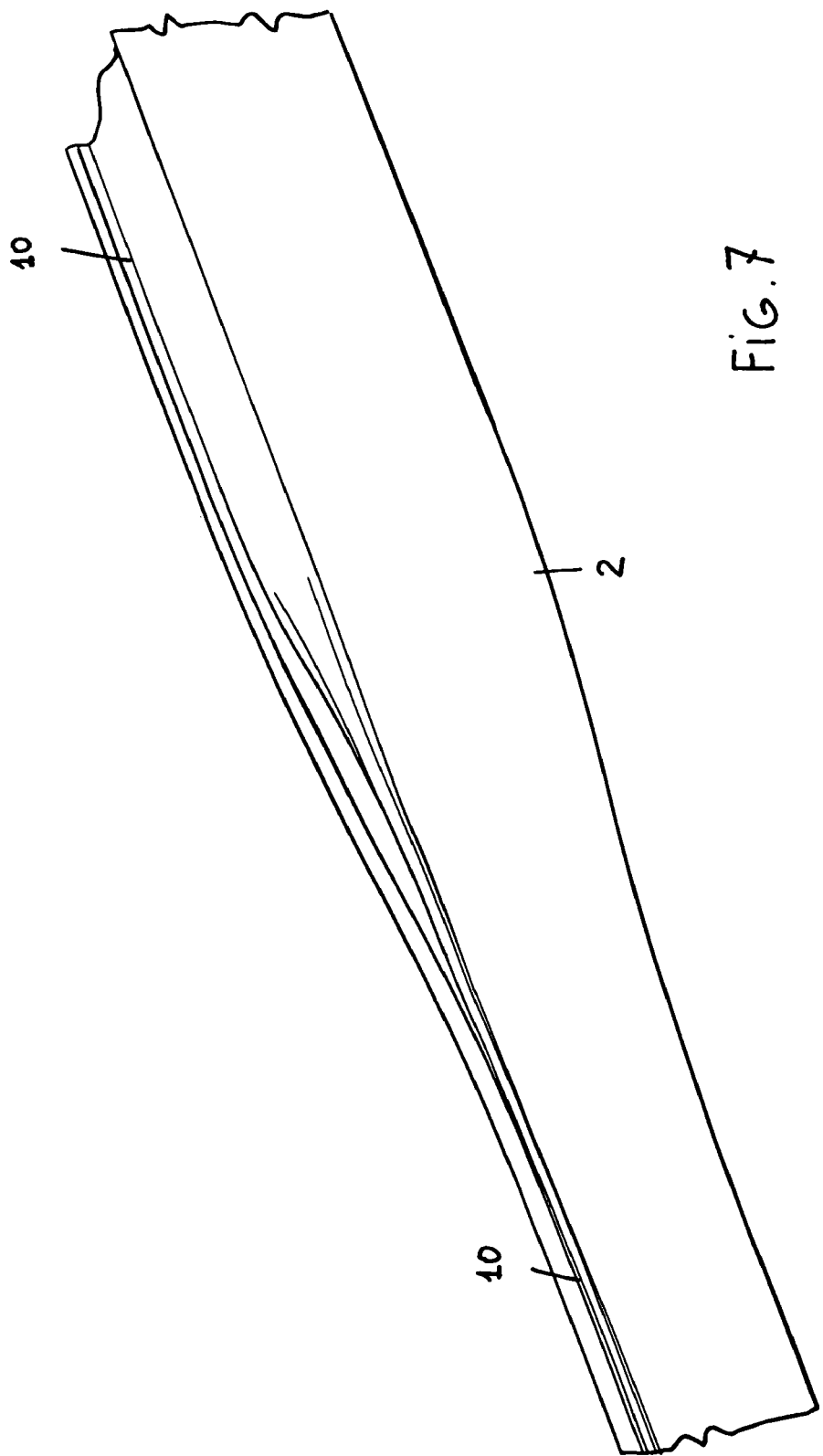
FIG. 7 is a further perspective view, on an enlarged scale, showing an enlarged region of the inserter tube and a still closed region thereof.
Figure 8:
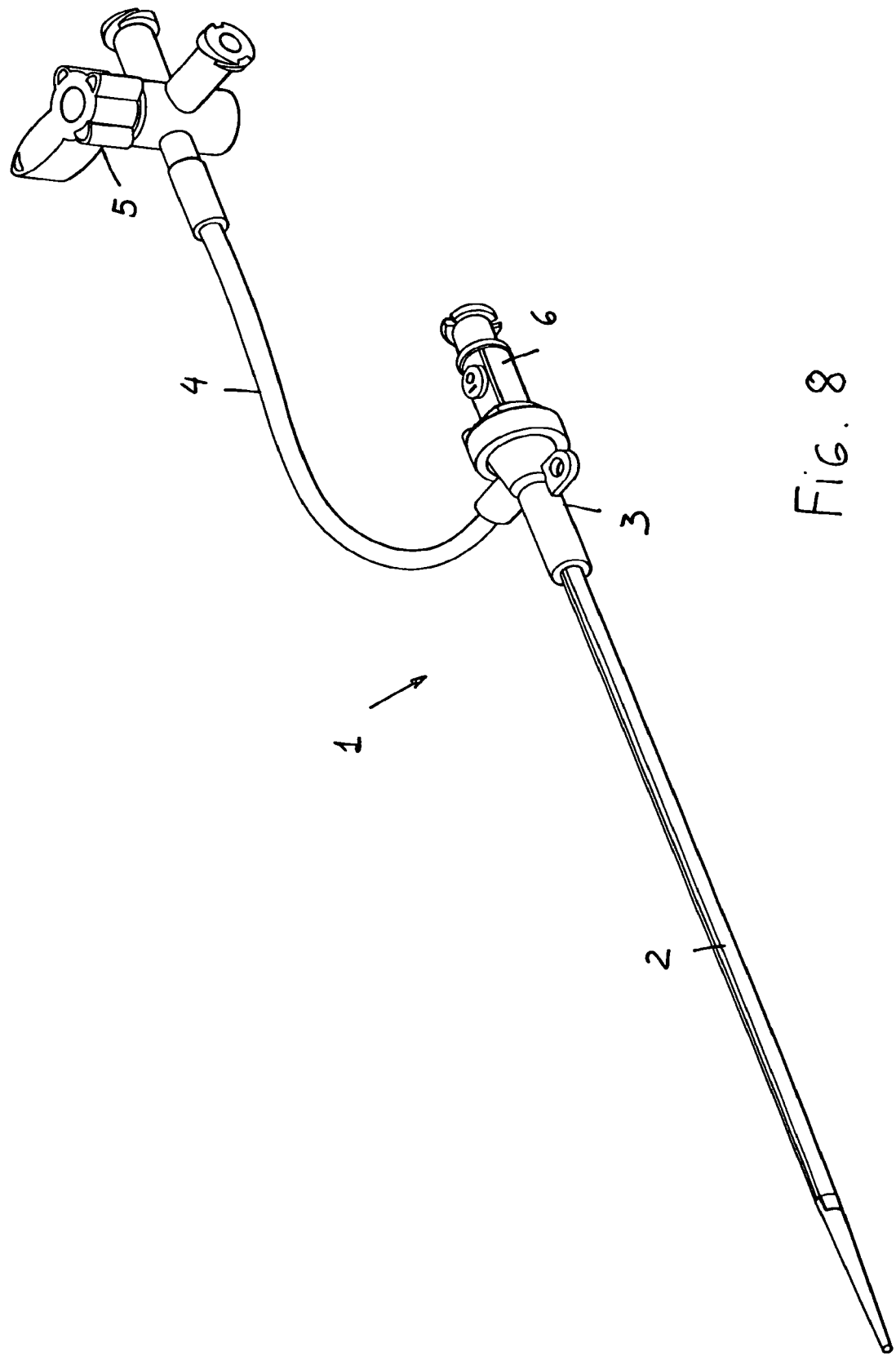
FIG. 8 is a perspective view showing the inserter as substantially stretched through the overall length thereof.

The end portion 11 of the tube has a tapering arrangement, as is better shown in FIG. 5, thereby it will be atraumatic for the vessel it is introduced into.

Thus, during a surgical procedure with a peripheral approaching, the inserter 1 will be arranged into the vessel by a standard operation and being therein held or used for a target time.

If the inserter must be used with an enlarged diameter, then a suitable dilatator will be engaged therein (for example 2.5 or 2.7 or 3 mm).

Thus, the dilatator will "open" the tube 2 thermoformed region, thereby moving away the edges of the recess or hollow 9.

Accordingly, the opening will be not performed to the possible maximum diameter, but to a diameter as set by the dilatator 6 or 66.

In particular, the opening will be performed in a gradual manner, from the valve 3 to the inserter tip 11, as is schematically shown in figures from 6 to 8.

As the tube 2 is stretched or enlarged through the overall length thereof, the dilatator 6 will be removed, and the inserter will be held at the achieved diameter.

Accordingly, the target device can be introduced or engaged without removing the inserter 1.

In particular, the inserter tube 2, in its stretched or enlarged condition, cannot further reduce its diameter.

Figure 9:
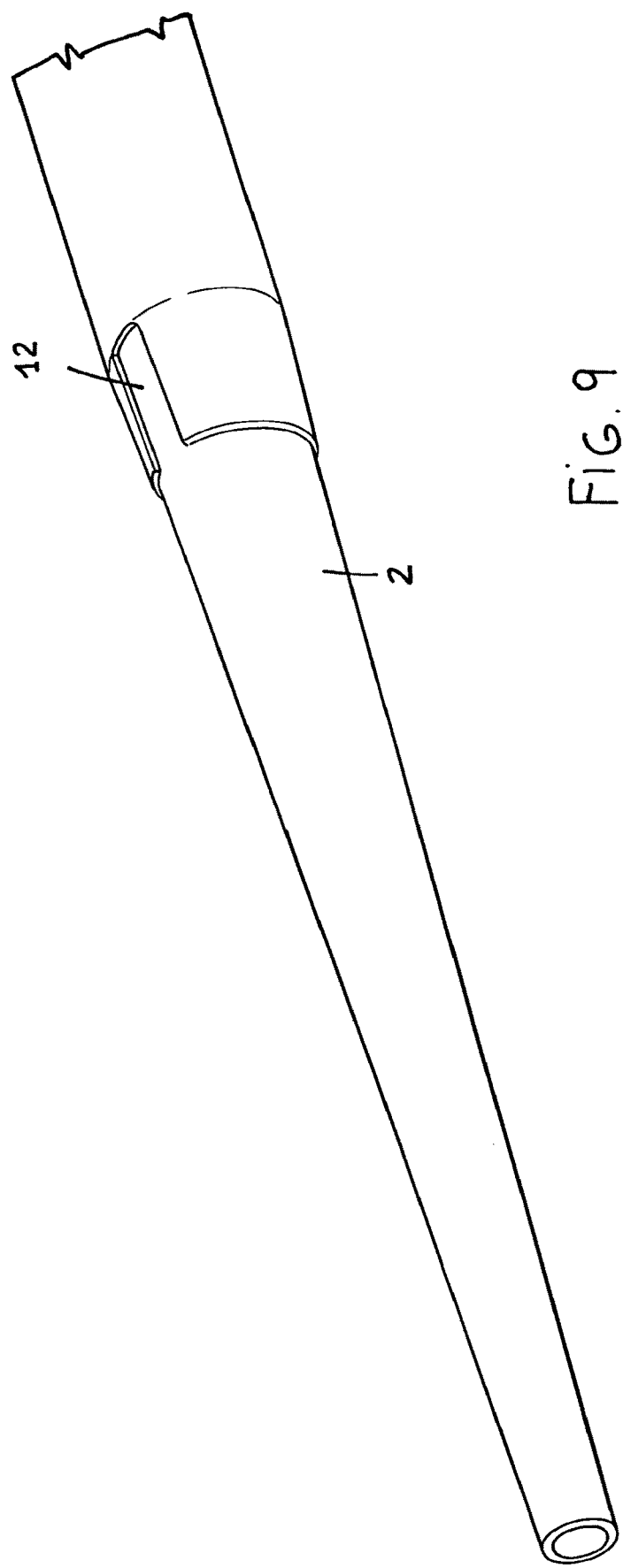
FIG. 9 shows an end opened portion of the inserter.
Figure 10:
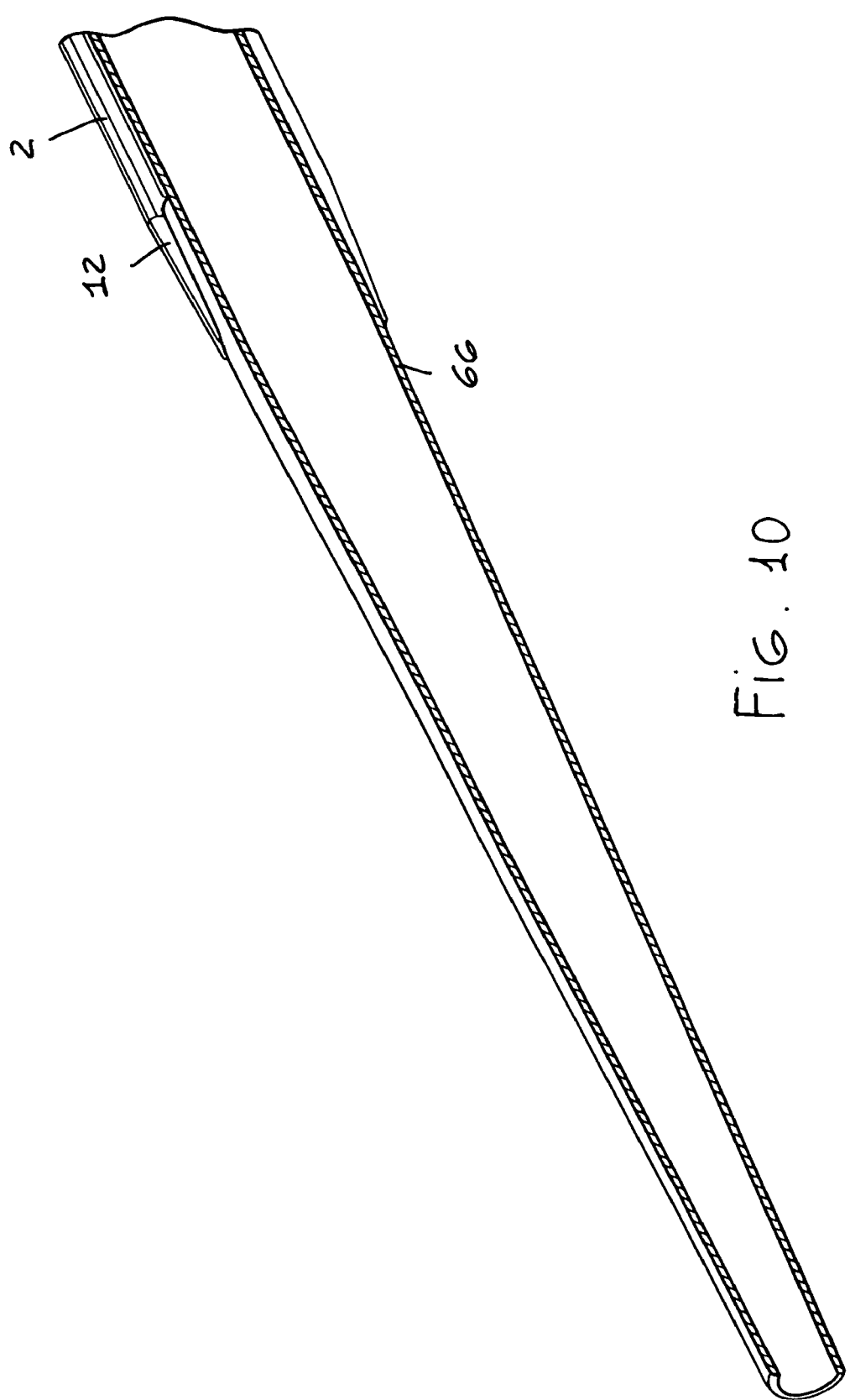
FIG. 10 is a further cross-sectional view of the inserter stretched by a large dilatator.

The inserter tapering tip 11 can lack material at the recess region, as indicated by the reference number 12, for meeting any making requirements, as is shown in FIGS. 9 and 10.

Actually, said tapering tip 11 can provide material lacking at the small thickness region.

It has been shown that the diameter increase in an artery does not generate any lesion damage to the artery, owing to the vessel wall resilient properties, preventing any lesions from occurring.

Moreover, the use of a dilatator having a diameter larger than the target diameter will be prevented by the valve 3, which is designed depending on the target maximum diameter size (for example 3 mm).

It has been found that the invention fully achieves the intended aim and objects.

In fact, the invention provides an inserter which is adapted to gradually increase its diameter up to a preset and constant maximum diameter.

On the contrary, the tubes made by prior medical devices had a fixed diameter and were constructed by extruding, molding, blowing, immersing procedures, and were either of a simple type or of a metal coil reinforced type.

The present invention provides a stretching diameter rigid tube which can be advantageously used as an inserter in the medical field.

The use of the novel stretching diameter inserter according to the present invention greatly improves the inserting procedure thereof thereby providing, for example, the following advantages:

a reduction of the material necessary to perform the procedure;
 a reduction of the operating time;
 a reduction of bleeding due to the inserter replacement operations;
 a reduction of possible risks associated with a relocation of an inserter;
 a reduction of any vasal traumas due to repeated punctures;
 a great facilitation of the puncture situ closure;
 the possibility of the easily fitting an inserter to a different size devices to be introduced, provided that the latter have a larger diameter.

In practicing the invention, the used materials, as well as the contingent size and shapes, can be any, depending on requirements.

The invention claimed is:

1. An inserter assembly comprising:
   an inserter comprising:
     a body comprising:
       a lumen extending along an axis therein the body further consisting of a single layer of a single material having a radially outermost surface and a radially innermost surface, the outermost surface configured to directly contact a patient's body while the inserter is in use,
       a region having a first wall thickness, and
       at least one longitudinally extending portion that defines a region of a second wall thickness, the second wall thickness reduced with respect to the first wall thickness and the second wall thickness forming a recess when the at least one longitudinally extending portion is in a final expanded configuration, the recess extending only partially through the single layer from the radially outermost surface of the body towards the radially innermost surface of the single layer,
       wherein the second wall thickness is defined by a portion of an outside wall surface disposed radially inward toward an inside wall surface, the portion of the outside wall surface extending annularly around the body in one direction from a first end of the recess to a second end of the recess, wherein the region having the first wall thickness extends annularly around the body in the other direction from the first end of the recess to the second end of the recess, and wherein the at least one longitudinally extending portion is folded on itself and radially outward with respect to itself in an initial folded configuration.

2. The inserter assembly of claim 1, wherein the at least one longitudinally extending portion is configured to transition from the initial folded configuration to the final expanded configuration.

3. The inserter assembly of claim 2, wherein an inside diameter of the inserter in the initial folded configuration is 5 French and the inside diameter of the inserter in the final expanded configuration is 8 French.

4. The inserter assembly of claim 3, wherein the inside diameter of the inserter is incrementally expandable between 5 French and 8 French.

5. The inserter assembly of claim 2, wherein the inserter is incrementally expandable between the initial folded configuration and the final expanded configuration.

6. The inserter assembly of claim 2, wherein the inserter plastically expands between the initial folded configuration and the final expanded configuration, such that the inserter maintains the final expanded configuration after transition between the initial folded configuration and the final expanded configuration.

7. The inserter assembly of claim 1, wherein the body comprises PE.

8. The inserter assembly of claim 1, wherein the body comprises FEP along an inside surface of the lumen.

9. The inserter assembly of claim 1, wherein the body further comprises a tapered tip.

10. The inserter assembly of claim 1, further comprising:
a first dilator; and
a second dilator;
wherein the first dilator is sized to be slidably inserted into the lumen without stretching the at least one longitudinally extending portion when the inserter is disposed in the initial folded configuration; and
wherein the second dilator is sized to circumferentially stretch the at least one longitudinally extending portion when the first dilator is inserted into the lumen when the inserter is disposed in the initial folded configuration to transition the inserter from the initial folded configuration to the final expanded configuration.

11. The inserter assembly of claim 10, wherein at least one of the first dilator and the second dilator comprises a tapered tip.

12. The inserter assembly of claim 1, wherein the at least one longitudinally extending portion does not extend past the radially outermost surface when in the initial folded configuration such that the outermost surface of the body maintains a substantially circular shape.

13. The inserter assembly of claim 12, wherein the at least one longitudinally extending portion comprises a single fold when in the initial folded configuration.

14. The inserter assembly of claim 13, wherein the single fold comprises an inverted U-shape.

15. The inserter assembly of claim 1, wherein the at least one longitudinally extending portion comprises a continuous single-layered annular wall extending entirely around the lumen when the at least one longitudinally extending portion is in the initial folded configuration.

16. A method of expanding an inserter comprising:
obtaining an inserter disposed in an initial folded configuration defining a first inside diameter;
advancing the inserter into a patient such that a radially outermost surface of the inserter directly contacts the patient's body; and
disposing a secondary element within a lumen of the inserter, an outside diameter of the secondary element being larger than the first inside diameter, to expand the inserter from the first inside diameter to a second inside diameter;
wherein expanding the inserter from the first inside diameter to the second inside diameter comprises displacing adjacent radially outward folded portions of a region of reduced wall thickness that forms a recess when the inserter is disposed in a final expanded configuration, wherein the recess extends only partially through a body of the inserter from the radially outermost surface of the inserter towards a radially innermost surface of the inserter the body consisting of a single layer of a single material, and
wherein the radially outward folded portions are formed of a continuous single-layered annular wall when the inserter is disposed in the initial folded configuration.

17. The method of claim 16, wherein expanding the inserter from the first inside diameter to the second inside diameter comprises expanding a proximal portion of the inserter prior to expanding a distal portion of the inserter.

18. The method of claim 16, wherein the inserter maintains the second inside diameter after withdrawal of the secondary element.

19. The method of claim 16, wherein the adjacent radially outward folded portions include a single fold comprising an inverted U-shape when in the initial folded configuration.

20. The method of claim 19, wherein the adjacent radially outward folded portions do not extend past the radially outermost surface when in the initial folded configuration such that the radially outermost surface of the inserter maintains a substantially circular shape.

* * * * *